United States Patent [19]

Behrens

[11] Patent Number: 5,002,954
[45] Date of Patent: Mar. 26, 1991

[54] BENZOTHIENOBENZACRIDINE-7-CARBOXYLIC ACIDS AS CANCER CHEMOTHERAPEUTIC AGENTS

[76] Inventor: Carl H. Behrens, 2140 Brandywood Dr., Wilmington, Del. 19810

[21] Appl. No.: 473,507

[22] Filed: Feb. 1, 1990

Related U.S. Application Data

[62] Division of Ser. No. 301,379, Jan. 25, 1989, Pat. No. 4,918,077.

[51] Int. Cl.$^5$ .................. A61K 31/44; C07D 221/02
[52] U.S. Cl. .................................. 514/279; 546/41
[58] Field of Search ...................... 514/279; 546/41

[56] References Cited

U.S. PATENT DOCUMENTS 2,579,420  12/1951  Doles .................................. 546/170
4,680,299  7/1987  Hesson ................................. 514/311

OTHER PUBLICATIONS

Buu-Hoï, et al Bull. Soc. Chem. 11, 127-36 (1944)
Chemical Abstracts, vol. 40, 1946, Abstract 2816.
Cromwell, et al J. Org. Chem. vol. 23, 1958, pp. 789 to 793.
Al-Tai, et al Bull. Coll. Sci (Baghdad) 9, 55-8 1966
Chemical Abstracts, vol. 68, 1968, Abs.:39436a.
Buu-Hoï, et al J. Chem. Soc. London, 1964, pp. 5622-5626.
Buu-Hoï, et al J. Chem. Soc. London 1963 pp. 2274-2279.
Braunholtz, et al J. Chem. Soc. London 1958 pp. 3368-3377.
Rosowsky, et al J. Heterocyclic Chem. Oct. 1971, pp. 809-820.
Cromwell J. Heterocyclic Chem. 16, 699 (1979).
Cromwell J. Org. Chem. 24, 1959 pp. 1077-1080.

Primary Examiner—Mukund J. Shah
Assistant Examiner—E. C. Ward

[57] ABSTRACT

Dihydrobenz[c]acridine carboxylic acid derivatives are provided which are useful in treating tumors in mammals. These dihydrobenz[c]acridine carboxylic acid derivatives have the formula:

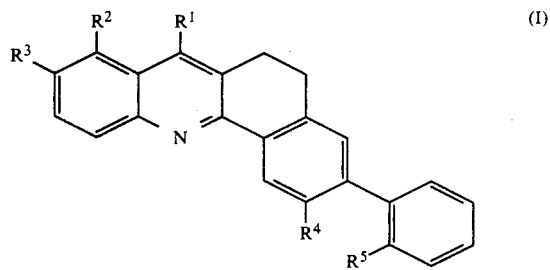

or a pharmaceutically acceptable salt thereof, where $R^1$, $R^2$, $R^3$, $R^4$ and $R^5$ are as defined in the specification. Also provided are pharmaceutical compositions of said compounds. In addition, processes for the preparation of these compounds are disclosed.

21 Claims, No Drawings

BENZOTHIENOBENZACRIDINE-7-CARBOXYLIC ACIDS AS CANCER CHEMOTHERAPEUTIC AGENTS

This is a division of application Ser. No. 07/301,379, filed Jan. 25, 1989 now U.S. Pat. No. 4,918,077.

BACKGROUND OF THE INVENTION

1. Field of the Invention

This invention relates to tumor inhibiting pharmaceutical compositions, methods of inhibiting the growth of mammalian tumors, and 3-phenyl-5,6-dihydrobenz[c]acridine-6-carbosylic acids and derivatives thereof useful in such compositions and methods.

2. Prior Art 5,6-dihydrobenz[c]acridine-7-carboxylic acids are well-known in the chemical literature. They are generally synthesized by the Pfitzinger reaction of an appropriate isatin with an appropriate 3,4-dihydro-1(2H)-naphthalenone.

Buu-Hoi et al. [Bull. Soc. Chim. 11, 127–136 (1944): Chem. Abstr. 40:2816] report the synthesis of 7-cyclohexyl-3,4-dihydro-1(2H)-naphthalenone and its reaction with isatin.

U.S. Pat. No. 2,579,420, issued to Coles on Dec. 18, 1951, describes the conversion of 6,8-dihalocinchonic acids into 6-halo-8-hydroxy cinchonic acids useful as color formers. The patent also discloses the Pfitzinger reaction of 3,4-dihydro-1(2H)-naphthalenone with substituted or unsubstituted 5,7-dihaloisatinic acids.

Cromwell et al. [J. Org. Chem. 23, 789–793 (1958) and J. Org. Chem. 24, 1077–1080 (1959)] report the synthesis of 5,6-dihydrobenz[c]acridine-7carboxylic acids as intermediates in the synthesis
of potential carcinogenic and/or antitumor benz[c]acridines.

Braunholtz et al. [J. Chem. Soc. 3368–3377 (1958)] report the synthesis of 5,6-dihydrobenz[c]-acridine-7-carboxylic acid.

Buu-Hoi et al. [J. Chem. Soc. 2274–2279 (1963) and J. Chem. Soc. 5622–5626 (1964)] report the synthesis of benz[c]acridines as potential carcinogens.

Sy et al. [Bull. Chim. Soc. Fr. 5, 1308–1315 (1965)] report the synthesis of 5,6-dihydrobenz[c]-acridine-7carboxylic acids.

Al-Tai et al. [J. Chem. U.A.R. 10, 339–352 (1967)] report the Pfitzinger reaction of 3,4-dihydro-1(2H)-naphthalenones.

Cagniant et al. [Bull. Soc. Chim. Fr. 3, 985–991 (1969)] report the synthesis of 5,6-dihydro-4,9dimethylbenz[c]acridine-7-carboxylic acid.

Rosowsky et al. [J. Heterocycl. Chem. 8, 809–820 (1971)] report 7-benz[c]acridinemethanols as tetracyclic analogs of the 2-phenyl-4-quinoline-methanol antimalarials.

Cromwell et al. [J. Heterocycl. Chem. 16, 699–704 (1979)] report the synthesis of 7-substituted-5,6-dimethylbenz[c]acridines as potential carcinogenic, carcinostatic, or antiparasitic agents.

U.S. Pat. No. 4,680,299, issued to Hesson on July 14, 1987, discloses tumor-inhibiting 2-phenyl-4-quinolinecarboxylic acids.

There are no literature references disclosing the 3-phenyl-5,6-dihydrobenz[c]acridine-7-carboxylic acids or derivatives thereof of this invention, or their use in inhibiting the growth of mammalian tumors.

SUMMARY OF THE INVENTION

According to the present invention there are provided dihydrobenz[c]acridine carboxylic acid derivatives of the formula:

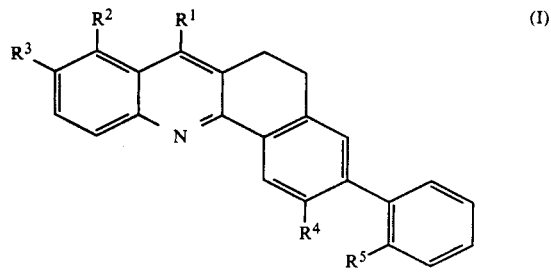

or a pharmaceutically acceptable salt thereof, wherein:
$R^1$ is $CO_2H$, $CO_2Na$, $CO_2K$, or $CO_2R^6$;
$R^2$ and $R^3$ independently are H, G, Cl, Br, I, $CH_3$, $CH_2CH_3$, $CF_3$, or $S(O)mR^7$;
$R^4$ and $R^5$ independently are H, or taken together are S with the proviso that when $R^1$ is $CO_2Na$ then $R^3$ is not F;
$R^6$ is $(CH_2)_nNR^8R^9$;
$R^7$ is alkyl of 1 to 5 carbon atoms optionally substituted with 1 or 2 of F, Cl and Br;
$R^8$ and $R^9$ independently are H or alkyl of 1 to 3 carbon atoms;
m is 0 to 2; and
n is 2 to 4.

Also provided are pharmaceutical compositions consisting essentially of a pharmaceutically acceptable carrier and one of the aforesaid compounds of Formula (I).

Further provided are methods of treating a tumor in a mammal which comprise administering a compound of Formula (I) to a mammal.

Still further provided are processes for preparing compounds of Formula (I) as described hereinafter.

PREFERRED EMBODIMENTS

Preferred compounds are those compounds of Formula (I) where:
(a) $R^1$ is $CO_2H$ or $CO_2Na$; and/or
(b) $R^2$ is H or Cl; and/or
(c) $R^3$ is H, F or Cl.

More preferred compounds are preferred compounds where:
(a) $R^2$ is H; and/or
(b) $R^3$ is H or F.

Specifically preferred compounds are:
(a) 5,6-Dihydro-3-phenylbenz[c]acridine-7-carboxylic acid, or a sodium salt;
(b) 5,6-Dihydro-9-fluoro-3-phenylbenz[c]acridine-7-carboxylic acid, or a sodium salt;
(c) 6,7-Dihydro-3-fluoro-[1]-benzothieno[2',3':4,5-]benz[1,2-c]acridine-5-carboxylic acid, or a sodium salt; and
(d) 6,7-Dihydro-[1]-benzothieno[2',3': 4,5]-benz[1,2-c]acridine-5-carboxylic acid, or a sodium salt.

DETAILED DESCRIPTION OF THE INVENTION

Synthesis

The compounds of Formula (I) wherein $R^4$ and $R^5$ are H can be prepared according to the route shown in Scheme 1. 3-(2-Dibenzothienoyl)propanoic acid (2) and 4-(2-benzothienyl)butanoic acid (3) have been reported by Gilman et al. [J. Org. Chem. 3, 108 (1938)]. The keto acid (2) can be prepared by the Friedel-Crafts acylation of dibenzothiophene (1) with succinic anhydride in the presence of a suitable Lewis acid such as $AlCl_3$ in an appropriate solvent such as methylene chloride at a temperature from 0° C. to the boiling point of the solvent. The Friedel-Crafts acylation is well-known in the chemical literature [House, H. O.; *Modern Synthetic Reactions*, 2nd Ed., W. A. Benjamin, 1972, pp. 786].

H. O.; *Modern Synthetic Reactions*, 2nd Ed., W. A. Benjamin, 1972, pp. 809].

Alternatively, the acid (4) may be converted to the corresponding acid chloride by the reaction with a reagent such as thionyl chloride, and the acid chloride may be cyclized with a Lewis acid such as $AlCl_3$ in a solvent such as carbon disulfide under Friedel-Crafts conditions.

The 3-phenyl-5,6-dihydrobenz[c]acridine-7-carboxylic acids (7) of Formula (I), can be prepared by the Scheme 1

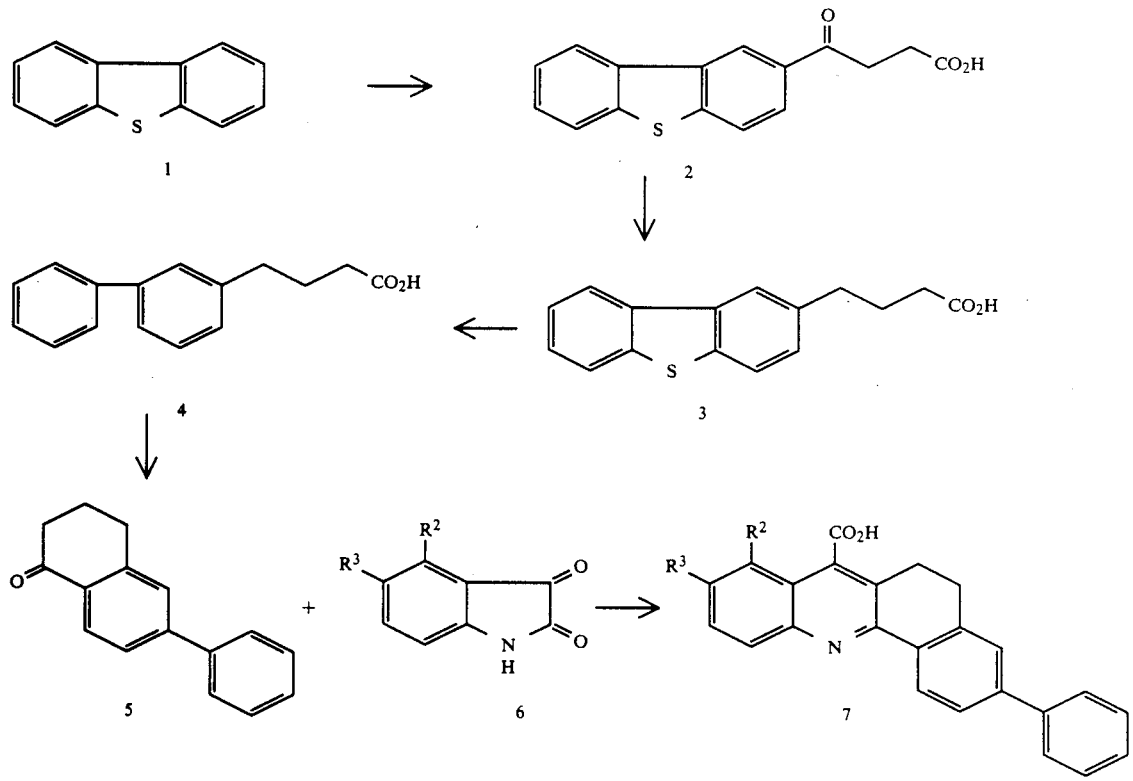

The acid (3) can be prepared by the Clemmensen reduction of (2) with zinc metal and hydrochloric acid in an appropriate solvent such as toluene-acetic acid at a temperature from room temperature to the boiling point of the solvent. The Clemmensen reduction is well-known in the chemical literature [House, H. O.; *Modern Synthetic Reactions*, 2nd Ed., W. A. Benjamin, 1972, pp. 163].

4-(3-Biphenylyl)butanoic acid (4) and 6-phenyl-3,4-dihydro-1(2H)-naphthalenone (5) have been reported by Lyle et al. [J. Org. Chem. 44, 4933-4938 (1979)]. The acid (4) can be prepared by the desulfurization of (3) with Raney nickel in an appropriate solvent such as aqueous sodium hydroxide at a temperature from room temperature to the boiling point of the solvent. Raney nickel is well-known in the chemical literature as a reducing agent for carbon-sulfur bonds.

The 3,4-dihydro-1(2H)-naphthalenone (5) can be prepared by the cyclization of the acid (4) in methanesulfonic acid at a temperature from room temperature to the boiling point of the solvent. Alternate acid catalysts such as polyphosphoric acid may be used in the cyclization of (4) to (5). The cyclization of 4-(phenyl)butanoic acids is well known in the chemical literature [House, Pfitzinger reaction of the isatins (6) with (5) in an appropriate solvent such as aqueous sodium or potassium hydroxide in ethanol at a temperature from room temperature to the boiling point of the solvent. Isatins (6) are commercially available or are prepared by the methods of Papp and references given therein [Adv. Heterocyclic Chem. 18, 1 (1975)]. The Pfitzinger reaction is well-known in the chemical literature.

The compounds of Formula (I) wherein $R^4$ and $R^5$ taken together represent S can be prepared according to the route shown in Scheme 2. The ketone (8) can be prepared by the cyclization of the acid (3) in methanesulfonic acid at a temperature from room temperature to the boiling point of the solvent. Other acid catalysts such as polyphosphoric acid may be used in the cyclization of (3) to (8). Alternatively, the acid (3) may be converted to the corresponding acid chloride by the reaction with a reagent such as thionyl chloride, and the acid chloride may be cyclized with a Lewis acid such as $AlCl_3$ in a solvent such as carbon disulfide under Friedel-Crafts conditions.

The 3-phenyl-5,6-dihydrobenz[c]acridine-7-carboxylic acids (9) of Formula (I) can be prepared by the Pfitzinger reaction of the isatins (6) with (8) as described above for the preparation of the compounds of Formula (7) in Scheme 1.

Scheme 2

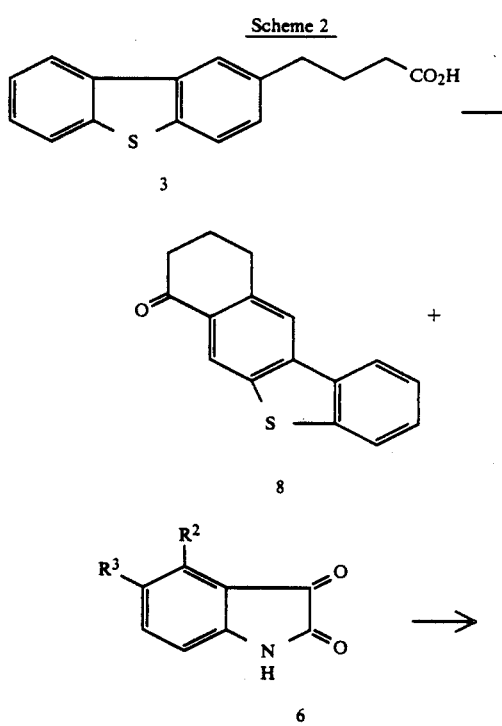

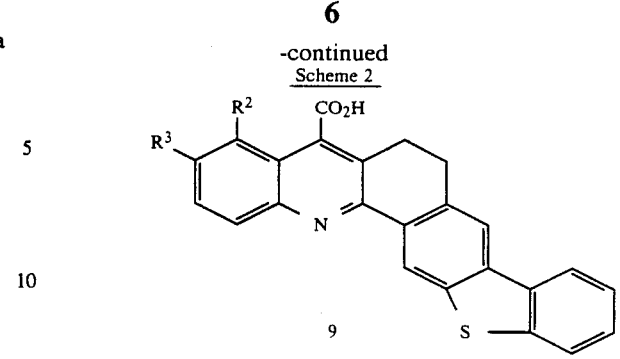

The compounds of Formula I wherein $R^1$ is $CO_2Na$ or $CO_2K$ can be prepared as shown in Scheme 3. The carboxylic acid (10) is treated with sodium hydroxide or potassium hydroxide in a suitable protic solvent such as ethanol at a temperature from room temperature to the boiling point of the solvent to afford the carboxylic acid salt (11).

The compounds of Formula I wherein $R^1$ is $CO_2R^6$ can be prepared as shown in Scheme 3. The carboxylic acid (10) is first converted to the corresponding acid chloride by the reaction with thionyl chloride or oxalyl chloride, either neat or in a suitable solvent such as methylene chloride or benzene, at a temperature from room temperature to the boiling point of the solvent. The ester (12) is prepared by the reaction of the intermediate acid chloride with the alcohol $R^6OH$ in a solvent such as tetrahydrofuran at a temperature from 0° C. to the boiling point of the solvent. The reaction of the acid chloride with $R^6OH$ is optionally in the presence of a base such as pyridine, trimethylamine, or 4-dimethylaminopyridine. Alternatively, the carboxylic acid salt (11) can be converted to the ester (12) as described above for the conversion of the acid (10) to the ester (12).

Scheme 3

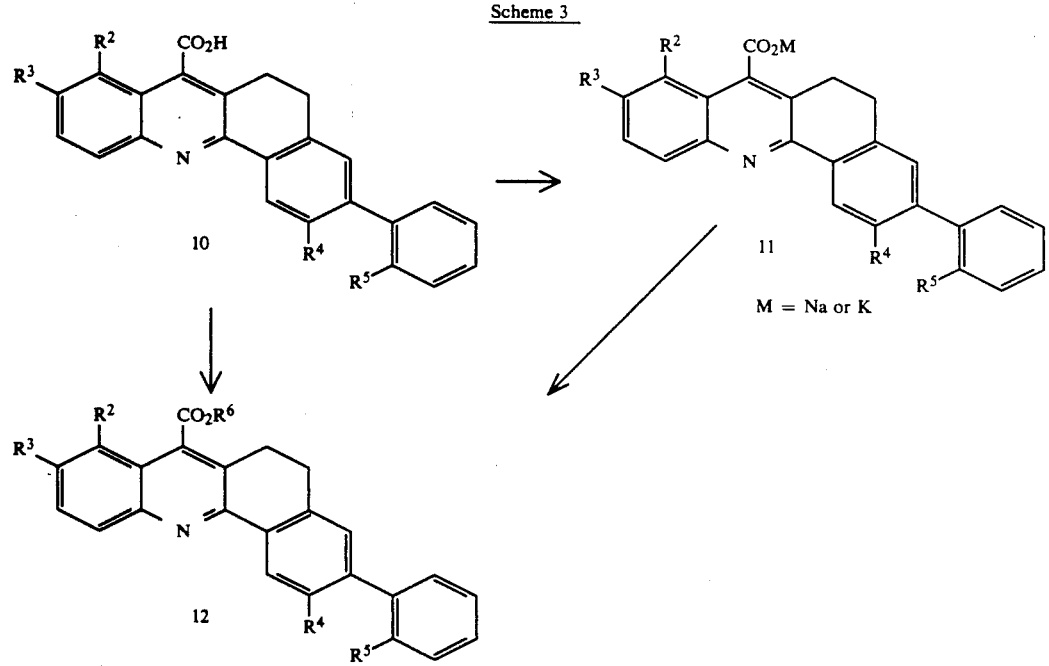

The preparation of pharmaceutically acceptable salts of the compounds of Formula (I) can be in accordance with well-known techniques of forming salts.

The compounds of this invention and their preparation can be further understood by the following examples, which do not constitute a limitation of the invention. In these examples, all temperatures are in degrees Centigrade unless otherwise specified. All melting points are uncorrected. All reactions were conducted in dry glassware under a nitrogen atmosphere except where otherwise noted. All commercial chemicals were used as received. Chromatography was performed with Merck silica gel 60 (230–400 mesh). The chromatography eluents are given as ratios by volume. Peak positions for $^1$H NMR spectra are reported as parts per million ($\delta$) downfield from the tetramethylsilane internal standard in organic solvents, and from the sodium 3-(trimethylsilyl)-1-propanesulfonate internal standard in deuterium oxide. Abbreviations for $^1$H NMR spectra are as follows: s=singlet, d=doublet, and m=multiplet.

EXAMPLE 1

Preparation of
5,6-Dihydro-3-phenylbenz[c]acridine-7-carboxylic acid

Part A

A 500-mL, three-necked, round-bottomed flask equipped with a reflux condenser, mechanical stirrer, and a thermometer was charged with a solution of dibenzothiophene (25.0 g, 135.7 mmol) in nitrobenzene (55 mL) and 1,1,2,2-tetracholorethane (110 mL). The reaction mixture was maintained at $-5°$ to $+5°$ by periodic cooling with a dry ice-acetone bath, while anhydrous aluminum chloride (53.6 g, 402 mmol) was added portionwise as a solid. After complete addition, the dark brown reaction mixture was maintained at 5° for 2 hours, and then it was allowed to gradually warm to room temperature overnight. The reaction mixture was quenched by cautiously pouring it into excess concentrated HCl and ice. The aqueous phase was extracted with methylene chloride. The combined organic extracts were concentrated, dissolved in aqueous sodium hydroxide, and extracted with ether to remove most of the neutral organic material. The aqueous phase was acidified to pH 1 with concentrated HCl, and the precipitate was collected by filtration. The precipitate was recrystallized from 50:1 ethyl acetate-methanol and then recrystallized from ethyl acetate to afford 3-(2-dibenzothienoyl)-propanoic acid (3.84 g, 13.51 mmol, 9.9% yield) as a white solid. The mother liquid was concentrated and the residue was recrystallized from ethyl acetate to afford a second crop (4.46 g, 15.69 mmol, 11% yield) as a white solid: mp 157°–158°; MS m/e 285(M$^+$+H); $^1$H NMR(acetone-d$^6$) $\delta$ 8.99(s,1H), 8.43–8.67(m,1H), 7.87–8.33(m,3H), 7.43–7.67(m,2H), 3.50(t,J=6 Hz,2H), 2.79(t,6 Hz,2H); HRMS m/e calcd for C$_{16}$H$_{12}$O$_3$S(M$^+$) 284.0508, Found 284.0505; Anal. Calcd for C$_{16}$H$_{12}$O$_3$S: C,67.59; H,4.25; S,11.28. Found: C,67.28; H,4.17; S,10.99.

Part B

A 1-L, round-bottomed flask equipped with a reflux condenser was charged with mossy zinc (50.0 g, 765 mmol) and then treated sequentially with mercury (II) chloride (5.0 g, 18.4 mmol), water (100 mL), and concentrated hydrochloric acid (2.5 mL). The reaction mixture was stirred for 5 minutes and the liquid was decanted to afford amalgamated zinc. To the freshly prepared amalgamated zinc was added sequentially water (38 mL), concentrated hydrochloric acid (88 mL), toluene (75 mL), acetic acid (3 mL), and the product of Part A (25.0 g, 80.0 mmol). The reaction mixture was heated at reflux for six days. Concentrated hydrochloric acid portions (25 mL) were added periodically over the six-day period. The reaction mixture was cooled and white crystals precipitated from the toluene. The precipitate was collected by suction filtration to afford 4-(2-dibenzothienyl)-butanoic acid (11.57 g, 42.80 mmol, 53% yield) as a white solid: mp 127°–128°; $^1$H NMR (CDCl$_3$) $\delta$ 8.00–8.17(m,1H), 7.80–8.00(m,1H), 7.67–7.79(m,2H), 7.33–7.50(m,2H), 7.17–7.32(m,1H), 2.85(t,J=7.5 Hz,2H), 2.42(t,J=7.5 Hz,2H), 1.93–2.17(m,2H); HRMS m/e calcd for C$_{16}$H$_{14}$O$_2$S(M$^+$) 270.0715, Found 270.0716.

Part C

A solution of the product of Part B (1.0 g, 3.70 mmol) in 10% aqueous sodium hydroxide (25 mL) was treated with 2-octanol (2 drops) as an antifoaming agent and Raney Nickel (11 g) as a slurry in pH 10 buffer and the reaction mixture was heated at 75° overnight. The hot reaction mixture was filtered through celite, and the celite was rinsed with hot 5% aqueous sodium hydroxide. The combined aqueous portions were acidified with concentrated hydrochloric acid and extracted with ether. The combined ether extracts were washed with saturated sodium chloride, dried, and concentrated to afford 4-(3-biphenyl)-butanoic acid (0.7 g, 2.9 mmol) as a white solid. This material was immediately dissolved in methanesulfonic acid (15 mL) and stirred at 40° overnight. The reaction mixture was cooled to room temperature, diluted with methylene chloride, washed with water, dried and concentrated. The residue was purified by flash chromatography with 10:1 hexane-ethyl acetate to afford 6-phenyl-3,4-dihydro-1(2H)-naphthalenone (0.18 g, 0.81 mmol, 22% yield) as a crystalline tan solid: mp 99°–100°; MS m/e 223(M$^+$+H); $^1$H NMR(CDCl$_3$) $\delta$8.10(d,J=8 Hz,1H), 7.27–7.67(m,7H), 3.03(t,J=6 Hz,2H), 2.68(t,J=6 Hz,2H), 2.17(m,2H); HRMS m/e calcd for C$_{16}$H$_{14}$O (M$^+$) 222.1045, found 222.1044.

Part D

A 250-mL, three-necked, round-bottomed flask equipped with a reflux condenser was charged with a suspension of isatin (1.1 g, 7.63 mmol) and the product of Part C (1.7 g, 7.63 mmol) in 6N KOH (48 mL) and absolute ethanol (48 mL). The purple-red mixture was heated at reflux overnight, cooled to 0° C. with an ice-water bath and poured portionwise with stirring into excess concentrated HCl and ice. The precipitate was filtered, washed with hot methanol (100 mL) and dried under high vacuum to afford the title compound (1.08 g, 3.07 mmol, 40% yield) as a yellow-green powder: mp 287°–290°; MS m/e 352(M$^+$+H), 308(M$^+$+H-CO$_2$); $^1$H NMR(DMSO-d$^6$) $\delta$ 8.54(d,J=8 Hz,1H), 8.14(d,J=8 Hz,1H), 7.56–7.86(m,7H), 7.41–7.52(m,3H), 3.11(s,4H); 1R(KBr pellet) 3400–1900(CO$_2$H), 1720(C=O), 1630, 1605, 1580, 1505 (arom C=C) cm$^{-1}$; HRMS m/e calcd for C$_{24}$H$_{17}$NO$_2$ (M$^+$) 351.1260, found 351.1253.

EXAMPLE 3

Preparation of
5,6-Dihydro-9-fluoro-3-phenylbenz[c]acridine-7-carboxylic acid

A 500-mL, three-necked, round-bottomed flask equipped with a reflux condenser was charged with a suspension of 5-fluoroisatin (3.27 g, 19.79 mmol) and the product of Example 1, Part C (4.40 g, 19.79 mmol) in 6N KOH (70 mL) and absolute ethanol (70 mL). The purple-red reaction mixture was heated at reflux overnight, cooled to room temperature and filtered. The filtrate was cooled to 0° with an ice-water bath and poured portionwise with stirring into excess concentrated HCl and ice. The yellow-brown precipitate was filtered, suspended in hot methanol, and filtered. The precipitate was then taken up in methylene chloride (200 mL), sonicated for 2.5 hours, and filtered to afford the title compound (5.70 g, 15.43 mmol, 78% yield) as a yellow powder: mp 309°-310°; MS m/e 370(M+ +H), 326(M+ +H—CO$_2$); $^1$H NMR(DMSO—d$^6$)δ 8.50(d,J=8Hz, 1H), 8.19(m,1H), 7.71-7.79(m,5), 7.41-7.56(m,4H), 3.68(s,4H); HRMS m/e calcd for C$_{24}$H$_{16}$NO$_2$F(M+) 369.1166, found 369.1180.

EXAMPLE 12

Preparation of
5,6-Dihydro-9-fluoro-3-phenylbenz[c]acridine-7-carboxylic acid, sodium salt A 100-mL, three-necked, round-bottomed flask equipped with a reflux condenser and an addition funnel was charged with a yellow suspension of the product of Example 3, (2.15 g, 5.82 mmol) in absolute ethanol (46 mL). The suspension was refluxed for 20 minutes and then 1 N sodium hydroxide (5.82 mL, 5.82 mmol) was added dropwise over 5 minutes. The orange solution was stirred at reflux for an additional 1.5 hours. The reaction mixture was then filtered while still warm, and the filtrate was concentrated and dried under high vacuum to afford the title compound (1.35 g, 3.45 mmol, 59% yield) as a light brown powder: mp >340°; $^1$H NMR(D$_2$O) δ 7.75(d,J=8.5 Hz, 1H), 7.55-7.70(m,1H), 7.35(d,J=8.5 Hz), 7.00-7.30(m,8H), 2.82(s,2H), 2.63(s,2H).

EXAMPLE 24

Preparation of 6,7-dihydro-[1]-benzothieno[2', 3':4,5]benz[1,2-c]-acridine-5-carboxylic acid]

A 200 mL, three-necked, round-bottomed flask equipped with a reflux condenser was charged with a suspension of isatin (580 mg, 3.94 mmole) and the product of Example 27, Part A (1.0 g, 3.94 mmole) in 6N KOH (52 mL) and absolute ethanol (52 mL). The reaction mixture was heated at reflux for 2.5 days. During this time, additional isatin (560 mg, 3.80 mmole) was added to drive the reaction to completion. The reaction mixture was cooled to 0° C. and poured into excess ice and concentrated hydrochloric acid. The brown precipitate was filtered. The product was dissolved in 5 % sodium hydroxide, extracted with ether to remove impurities, and precipitated with hydrochloric acid to afford the title compound (82 mg, 0.21 mmole, 5.4 % yield) as a green powder: mp 190° -193° ; MS m/e 382 (M+ +H), 338 (M+$_{30}$H-CO$_2$); $^1$H NMR (DMSO) 9.04(s, 1H), 8.40(s, 1H), 8.08-8.18(m,4H), 7.54-7.88(m, 4H), 3.19(s, 4H); HRMS m/e calcd for C$_{24}$H$_{15}$NO$_2$S (M+) 381.0824, found 381.0824.

EXAMPLE 27

Preparation of
6,7-Dihydro-3-fluoro-[1]-benzothieno[2',3':4,5-]benz[1,2-c]acridine-5-carboxylic acid Part A A 500-mL, three-necked, round-bottomed flask equipped with a reflux condenser and a thermometer was charged with the product of Example 1, Part B (10.0 g, 41.6 mmol) and methanesulfonic acid (200 mL). The dark brown suspension was heated to 40° overnight with stirring. The reaction mixture was cooled to 0° with an ice-water bath, poured into 150 g of ice, stirred for 15 min, and filtered to afford a green paste. This paste was purified by flash chromatography with methylene chloride to afford 9,10-dihydrobenzo[b]naphtho[2,3-d]thiophen-7(8H)-one (6.4 g, 41.6 mmol, 61% yield) as a yellow crystalline solid: mp 160°-165° ; MS m/e 253(M+ +H); $^1$H NMR (CDCl$_3$) δ 8.54(s, 1H), 8.14(dd,J=2Hz, J=6Hz, 1H), 7.98(3,1H), 7.80-7.90(m, 1H) 7.45-7.60(m,2H), 3.15(t,J=6Hz, 2H), 2.73(t,J=6Hz, 2H), 2.20(t,J=6Hz, 2H); Anal. Calcd for C$_{16}$H$_{14}$OS: C,75.56; H,5.55; S,12.61. Found: C,76.00; H,5.73; S,12.84.

Part B

A 500-mL, three-necked, round-bottomed flask equipped with a reflux condenser was charged with a suspension of 5-fluoroisatin (3.9 g, 23.62 mmol) and the product of Part A (6.0 g, 23.62 mmol) in 6 N KOH (70 mL) and absolute ethanol (70 mL). The purple-red reaction mixture was heated at reflux for two days, and filtered. The filtrate was concentrated and extracted with ether. The aqueous layer was poured into excess ice and concentrated HCl, stirred for 20 minutes, and filtered to afford an orange-yellow solid. The solid was suspended in hot methanol, filtered, suspended in boiling water (600 mL), filtered, washed with cold methanol, and dried under high vacuum. This solid was then suspended in methylene chloride (200 mL), sonicated for 2.5 hours, filtered, and dried to afford the title compound (2.0 g, 5.01 mmol, 21% yield) as a pale green solid: mp 280°-283° ; MS m/e 400(M+ +H); $^1$H NMR (DMF-d$^7$) δ9.06(s,1H), 8.44-8.48(m,1H), 8.39(s,1H), 8.24-8.28(m,1H), 8.06-8.11(m,1H), 7.54-7.74(m,4H), 3.26(s,4H); HRMS m/e calcd for C$_{24}$H$_{14}$NO$_2$FS (M+) 399.0730; Found 399.0701.

The compounds of Examples 1, 3, 12, 24, and 27, and other compounds which have been prepared using the procedures of Examples 1, 3, 12, 24, and 27, and other compounds which may be prepared by such procedures are listed in Tables 1 and 2.

TABLE 1

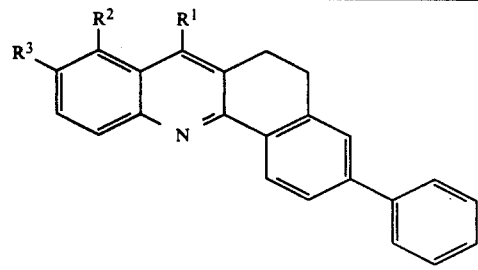

| Ex. | R$^1$ | R$^2$ | R$^3$ | mp (°C.) |
|---|---|---|---|---|
| 1 | CO$_2$H | H | H | 287-290° |
| 2 | CO$_2$H | Cl | H | |
| 3 | CO$_2$H | H | F | 309-310° |
| 4 | CO$_2$H | H | Cl | |
| 5 | CO$_2$H | H | Br | |
| 6 | CO$_2$H | H | I | |
| 7 | CO$_2$H | H | Me | |
| 8 | CO$_2$H | H | Et | |
| 9 | CO$_2$H | H | CF$_3$ | |
| 10 | CO$_2$Na | H | H | |
| 11 | CO$_2$K | Cl | H | |
| 12 | CO$_2$Na | H | F | >340° |
| 13 | CO$_2$K | H | Cl | |
| 14 | CO$_2$Na | H | Br | |
| 15 | CO$_2$K | H | I | |
| 16 | CO$_2$Na | H | Me | |
| 17 | CO$_2$Na | H | Et | |

TABLE 1-continued

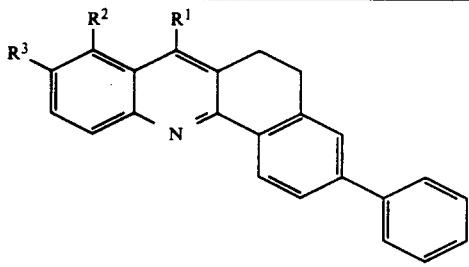

| Ex. | R¹ | R² | R³ | mp (°C.) |
|---|---|---|---|---|
| 18 | $CO_2Na$ | H | $CF_3$ | |
| 19 | $CO_2H$ | H | $SCH_3$ | |
| 20 | $CO_2H$ | H | $SOCH_3$ | |
| 21 | $CO_2H$ | H | $SO_2CH_3$ | |
| 22 | $CO_2CH_2CH_2N(CH_3)_2$ | H | H | |
| 23 | $CO_2CH_2CH_2N(CH_3)_2$ | H | F | |

TABLE 2

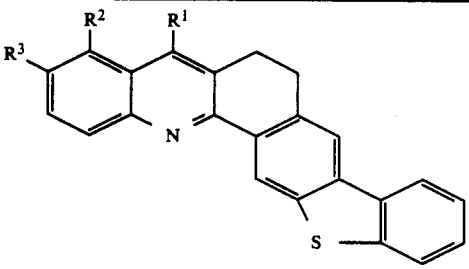

| Ex. | R¹ | R² | R³ | mp (°C.) |
|---|---|---|---|---|
| 24 | $CO_2H$ | H | H | 190–193 |
| 25 | $CO_2H$ | Cl | H | |
| 26 | $CO_2H$ | H | Cl | |
| 27 | $CO_2H$ | H | F | 280–283 |
| 28 | $CO_2H$ | H | Br | |
| 29 | $CO_2H$ | H | I | |
| 30 | $CO_2H$ | H | Me | |
| 31 | $CO_2H$ | H | Et | |
| 32 | $CO_2H$ | H | $CF_3$ | |
| 33 | $CO_2Na$ | H | H | |
| 34 | $CO_2K$ | Cl | H | |
| 35 | $CO_2Na$ | H | F | |
| 36 | $CO_2K$ | H | Br | |
| 37 | $CO_2Na$ | H | I | |
| 38 | $CO_2K$ | H | Me | |
| 39 | $CO_2Na$ | H | Et | |
| 40 | $CO_2K$ | H | $CF_3$ | |
| 41 | $CO_2H$ | H | $SCH_3$ | |
| 42 | $CO_2H$ | H | $SOCH_3$ | |
| 43 | $CO_2H$ | H | $SO_2CH_3$ | |
| 44 | $CO_2CH_2CH_2N(CH_3)_2$ | H | H | |
| 45 | $CO_2CH_2CH_2N(CH_3)_2$ | H | F | |

UTILITY

Results of the various biological tests described below establish that the compounds of this invention have the properties of inhibiting the growth of transplanted mouse tumors in mice, inhibiting the growth of human tumors implanted in mice and also inhibiting the growth of human melanoma tumor cells in vitro.

The efficacy of the compounds of this invention against transplanted mouse tumors was evaluated in test systems which are used by the National Cancer Institute for the detection and assessment of anticancer activity. Most clinically effective drugs exhibit activity in these tests and the tests have a good record of predicting clinical efficacy [Goldin, A., Venditti, J. M., MacDonald, J. S., Muggia, F. M., Henney, J. E. and V. T. Devita, Jr., Europ. J. Cancer, 17, 129–142, (1981); Venditti, J. M., Seminars in Oncology, 8(4) (1981); Goldin, A. and J. M. Venditti in Recent Results in Cancer Research, 70, S. K. Carter and Y. Sakurai, Eds., Springer-Verlag, Berlin/Heidelberg, 1980].

L1210 Murine Leukemia Test

The L1210 tumor line originated in 1948 as a lymphocytic leukemia in a female DBA/2 mouse after the skin was treated with 0.2% 20-methylcholanthrene in ethyl ether. The tumor line is maintained by serial passage in female DBA/2 mice.

On day 0, female $CDF_1$ mice weighing 18–22 g are inoculated with $1 \times 10^5$ L1210 leukemia cells harvested from the ascites of DBA/2 mice. The mice are randomized into groups of six each and the test compounds and vehicle control are administered intraperitoneally once daily for nine consecutive days beginning on day 1. A $\geq 20\%$ decrease in body weight on day 5 is considered an indication of toxicity. The acceptable control mean survival time is 8–11 days.

Results are expressed as a percentage of the mean survival time of the vehicle-treated control group according to the formula:

$$\% \text{ T/C} = \frac{\text{Mean survival time of treated}}{\text{Mean survival time of control}} \times 100\%.$$

Mice which survive for 30 days are considered cured and are not included in the calculation of the mean survival time.

The NCI criteria for activity is used. A compound is considered to have moderate activity against L1210 leukemia if it has a % T/C $\geq 125\%$, and it is considered to have good activity against L1210 leukemia if it has a % T/C $\geq 150\%$.

The results of tests with the compounds of this invention are shown in Table 3. The data indicate that the compounds of this invention are effective against the L1210 leukemia in mice.

TABLE 3

| Ex | 1210 Leukemia % T/C (dose: mg/kg) |
|---|---|
| 1 | 178% (100) |
| 3 | 180% (100) |
| 12 | 171% (50) |
| 27 | 149% (100) |

DLD-2 HUMAN COLON CARCINOMA XENOGRAFT TEST

The DLD-2 tumor line was originally obtained from a primary colon carcinoma surgically removed from a male patient. The line is maintained by serial passage in athymic nude mice.

On day 0, male and female outbred Swiss mice bearing the NU/NU gene and weighing 22–30 g are inoculated with 0.2 mL of a 25% tumor mince. This mince is prepared by mincing fresh DLD-2 tumors, grown subcutaneously in passage mice, in sterile physiological saline. Palpable tumors appear in 7–10 days and weigh approximately 50 mg. The mice are pair matched by tumor weight and sex into groups of ten each and the test compounds and vehicle control are administered intraperitoneally once daily for nine consecutive days. A $\geq 20\%$ decrease in body weight on day 5 is considered an indication of toxicity. Tumor measurements and weights are recorded once a week. Eighteen days after the initial injection, the mice are weighed, sacrificed, and the tumors excised and weighed.

The efficacy of the test compounds is determined by the extent of tumor growth inhibition in treated versus vehicle-treated control mice. Initial tumor weights (mg) are calculated from the tumor dimensions (mm) using the formula for the volume of a prolate ellipsoid ($LxW^2/2$). Net tumor weights are calculated for each of the treated groups and the vehicle-treated control group by subtracting the initial tumor weight (estimated) from the final tumor weight (actual) on day 19. The acceptable mean tumor weight for the control group is >1 g. Results are expressed as percent inhibition of control growth according to the formula:

$$\% \text{ Inhibition} = \frac{\text{Mean tumor weight of treated}}{\text{Mean tumor weight of control}} \times 100\%.$$

The NCI criteria for activity is used. A compound is considered to have moderate activity against DLD-2 colon carcinoma if it causes 58–89% inhibition of tumor growth, and it is considered to have good activity against DLD-2 colon carcinoma if it causes $\geq 90\%$ inhibition of tumor growth.

The results of tests with compounds of this invention are shown in Table 4. The data indicate that compounds of this invention are effective against the DLD-2 human colon carcinoma xenograft in mice.

TABLE 4

| Ex. | DLD-2 Human Colon Carcinoma Xenograft % Inhibition (dose: mg/kg) |
| --- | --- |
| 3 | 70% (50) |

B16 MURINE MELANOMA TEST

The B16 tumor line arose spontaneously in 1954 on the skin at the base of the ear of a C57BL mouse. The tumor line is maintained by serial passage in female C57BL mice.

On day 0, female B6C3F1 mice are inoculated intraperitoneally with 0.5 mL of a 10% tumor brei. This brei is prepared by homogenizing fresh B16 tumors, grown subcutaneously in C57BL mice, in cold physiological saline. Mice are randomized in groups of ten each, with 20 animals being in the control group. The test compounds and vehicle control are administered intraperitoneally once daily for nine consecutive days beginning on day 1. A $\geq 20\%$ decrease in body weight on day 5 is considered an indication of toxicity. The acceptable mean control survival time is 14–22 days. Results are expressed as a percentage of the mean survival time of the vehicle-treated control group according to the formula:

$$\% \ T/C = \frac{\text{Mean survival time of treated}}{\text{Mean survival time of control}} \times 100\%.$$

Mice which survive 90 days are considered cured and are not included in the calculation of the mean survival time.

The NCI criteria for activity is used. A compound is considered to have moderate activity against B16 melanoma if it has a % $T/C \geq 125\%$, and it is considered to have good activity against B16 melanoma if it has a % $T/C \geq 150\%$.

The results of tests with compounds of this invention are shown in Table 5. The data indicate that the compounds of this invention are effective against the B16 melanoma in mice.

TABLE 5

| Ex. | B16 Murine Melanoma % T/C (dose: mg/kg) |
| --- | --- |
| 3 | 134% (35) |
| 12 | 140% (50) |

IN VITRO RPMI-7272 HUMAN MELANOMA TEST

The compounds of this invention were also tested for their ability to inhibit the growth of human melanoma RPMI-7272 cells in vitro.

Human melanoma RPMI-7272 cells (Quinn et al. [J. Natl. Cancer Inst. 59, 301–305 (1977)]) are propagated in RPMI-1640 medium supplemented with 10 mM Tricine (pH 7.8), 10 mM HEPES (pH 7.3), 0.075% sodium bicarbonate, and 10% (vol/vol) heat-inactivated (56° C., 30 minutes) fetal bovine serum in a 95% air: 5% $CO_2$ humidified atmosphere. Cells are seeded at $3 \times 10^5$ per 35 mm plate to initiate growth inhibition studies. Cultures to receive growth medium only (control cultures) are set up in quadruplicate; cultures to receive varying concentrations of compounds are set up at one dish per dose of compound. Twenty-four hours post-seeding, duplicate control cell cultures are trypsinized and cells are counted using a Coulter Counter (day 1 control counts). At this time, varying concentrations of test compounds, from 100 to 0.00001 µg/mL are added to cultures and growth medium only is added to control cultures. Seventy-two hours after the addition of compound, cells are trypsinized and counted. The numbers of cell population doublings (day 4) in the presence or absence of compound are calculated.

The $ID_{50}$ represents the dose of compound (in µg/mL) required to inhibit the number of cell doublings by 50%. A compound is considered to have in vitro activity against RPMI-7272 melanoma if it has an $ID_{50}$ $\leq 10$ µg/mL. The number of population doublings of control cultures during 72 hours is between 3 and 4.

Compounds are dissolved at 10–25 mg/mL in dimethylsulfoxide. Dilutions to 1 mg/mL in complete growth medium are made, followed by stock preparations of 100 and 30 µg/mL in complete growth medium. Serial ten-fold dilutions in complete medium are formulated from the 100 and 30 µg/mL stocks, respectively, and added to cultures.

The results of tests with the compounds of this invention are shown in Table 6. The data indicate that the compounds of this invention are potent inhibitors of RPMI-7272 human melanoma cell growth in vitro.

TABLE 6

| Ex. | RPMI-7272 Melanoma $ID_{50}$ (µg/mL) |
| --- | --- |
| 1 | 14.1 |
| 3 | 0.05 |
| 12 | 0.06 |
| 24 | 1.96 |
| 27 | 1.4 |

DOSAGE FORMS

The antitumor compounds (active ingredients) of this invention can be administered to inhibit tumors by any means that produces contact of the active ingredient with the agent's site of action in the body of a mammal. They can be administered by any conventional means available for use in conjunction with pharmaceuticals; either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a tumor-inhibiting amount of active ingredient and will, of course, vary depending upon known factors such as the pharmacodynamic characteristics of the particular active ingredient, and its mode and route of administration; age, health, and weight of the recipient; nature and extent of symptoms; kind of concurrent treatment, frequency of treatment, and the effect desired. Usually a daily dosage of active ingredient can be about 5 to 400 milligrams per kilogram of body weight. Ordinarily, 10 to 200, and preferably 10 to 50, milligrams per kilogram per day given in divided doses 2 to 4 times a day or in sustained release form is effective to obtain desired results.

Dosage forms (compositions) suitable for internal administration contain from about 1.0 milligram to about 500 milligrams of active ingredient per unit. In these pharmaceutical compositions, the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzaalkonium chloride, methyl- or propyl-paraben, and chlorbutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 100 milligrams of powdered active ingredient, 175 milligrams of lactose, 24 milligrams of talc, and 6 milligrams magnesium stearate.

A mixture of active ingredient in soybean oil is prepared and injected by means of a positive displacement pump into gelatin to form soft gelatin capsules containing 100 milligrams of the active ingredient. The capsules are washed and dried.

TABLETS

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability of delay absorption.

INJECTABLE

A parenteral composition suitable for administration by injection is prepared by stirring 1.5% by weight of active ingredient in 10% by volume propylene glycol and water. The solution is made isotonic with sodium chloride and sterilized.

SUSPENSION

An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

"Consisting essentially of" in the present disclosure is intended to have its customary meaning: namely, that all specified material and conditions are very important in practicing the invention but that unspecified materials and conditions are not excluded so long as they do not prevent the benefits of the invention from being realized.

What is claimed is:

1. A compound having the formula:

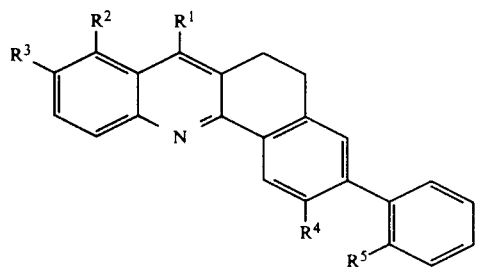

or a pharmaceutically acceptable salt thereof, wherein:
$R^1$ is $CO_2H$, $CO_2Na$, $CO_2K$, or $CO_2R^6$;
$R^2$ and $R^3$ independently are H, F, Cl, Br, I, $CH_3$, $CH_2CH_3$, $CF_3$, or $S(O)mR^7$;
$R^4$ and $R^5$ taken together are S with the proviso that when $R^1$ is $CO_2Na$ then $R^3$ is not F;
$R^6$ is $(CH_2)_nNR^8R^9$;

$R^7$ is alkyl of 1–5 carbon atoms optionally substituted with 1 or 2 substituents, independently selected from F, Cl and Br;

$R^8$ and $R^9$ independently are H or alkyl of 1–3 carbon atoms;

m is 0 to 2; and n is 2 to 4.

2. A compound of claim 1 wherein $R^1$ is $CO_2H$ or $CO_2Na$.

3. A compound of claim 1 wherein $R^2$ is H or Cl.

4. A compound of claim 1 wherein $R^3$ is H, F or Cl.

5. A compound of claim 1 wherein $R^1$ is $CO_2H$ or $CO_2Na$; $R^2$ is H or Cl; and $R^3$ is H, F or Cl.

6. A compound of claim 5 wherein $R^2$ is H.

7. A compound of claim 5 wherein $R^3$ is H or F.

8. A compound of claim 1 wherein $R^2$ is H and $R^3$ is H or F.

9. The compound of claim 1 which is 6,7-dihydro-3-fluoro-[1]-benzothieno[2',3':4,5]benz[1,2-[c]acridine-5-carboxylic acid, or a sodium salt thereof.

10. The compound of claim 1 which is 6,7-dihydro-[1]-benzothieno[2',3':4,5]benz[1,2-[c]acridine-5-carboxylic acid, or a sodium salt thereof.

11. A pharmaceutical composition comprising a pharmaceutically acceptable carrier and a compound of claim 1.

12. A pharmaceutical composition comprising a pharmaceutically acceptable carrier and a compound of claim 2.

13. A pharmaceutical composition comprising a pharmaceutically acceptable carrier and a compound of claim 3.

14. A pharmaceutical composition comprising a pharmaceutically acceptable carrier and a compound of claim 4.

15. A pharmaceutical composition comprising a pharmaceutically acceptable carrier and a compound of claim 5.

16. A pharmaceutical composition comprising a pharmaceutically acceptable carrier and a compound of claim 6.

17. A pharmaceutical composition comprising a pharmaceutically acceptable carrier and a compound of claim 7.

18. A pharmaceutical composition comprising a pharmaceutically acceptable carrier and a compound of claim 8.

19. A pharmaceutical composition comprising a pharmaceutically acceptable carrier and the compound of claim 9.

20. A pharmaceutical composition comprising a pharmaceutically acceptable carrier and the compound of claim 10.

21. A method of treating leukemia and : and melanoma tumor in a mammal comprising administering to the mammal an effective amount of any of the compounds of claim 1 to 10.

* * * * *